(12) United States Patent
Craik et al.

(10) Patent No.: US 7,001,883 B1
(45) Date of Patent: Feb. 21, 2006

(54) CYCLIZED CONOTOXIN PEPTIDES

(75) Inventors: David James Craik, Queensland (AU);
Norelle Lee Daly, Queensland (AU);
Katherine Justine Nielsen, Queensland (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/787,082

(22) PCT Filed: Sep. 14, 1999

(86) PCT No.: PCT/AU99/00769

§ 371 (c)(1),
(2), (4) Date: Jun. 14, 2001

(87) PCT Pub. No.: WO00/15654

PCT Pub. Date: Mar. 23, 2000

(30) Foreign Application Priority Data

Sep. 14, 1998 (AU) ...................................... PP5895

(51) Int. Cl.
*A61K 38/12* (2006.01)
*C07K 14/00* (2006.01)

(52) U.S. Cl. .............................. 514/9; 514/12; 514/13; 514/217; 530/317; 530/324; 530/326; 530/334; 530/344

(58) Field of Classification Search .................... 514/9, 514/12, 13, 21; 530/317, 324, 326, 334, 530/344
See application file for complete search history.

(56) References Cited

U.S. PATENT DOCUMENTS 4,447,356 A * 5/1984 Olivera et al. ......... 260/112.5 R
5,589,356 A 12/1996 Tam .......................... 435/68.1

FOREIGN PATENT DOCUMENTS

| WO | WO 96/33206 | 10/1996 |
|---|---|---|
| WO | WO 96/34878 | 11/1996 |
| WO | 98/03541 | 1/1998 |
| WO | 98/20026 | 5/1998 |
| WO | WO 98/28434 | 7/1998 |
| WO | WO 98/56807 | 12/1998 |

OTHER PUBLICATIONS

Pallaghy et al., Protein Science 3, 1833-1839 (1994).*
Al-Obeidi, F., et al., "Potent and prolonged acting cyclic lactam analogues of β-melanotropin: design based on molecular dynamics," *J. Med. Chem.,* 1989, 32, 2555-2561.
Armishaw, C.J., et al., "Synthesis of backbone cyclic analogues of β-conotoxin IMI by chemoselective ligation of unprotected linear precursors," Benedetti, E., et al. (Eds.), *Peptides,* 2002, 1 p. (Abstract).
Armishaw C.J., et al., "Synthesis of N to C terminal cyclic analogues of β-conotoxin IMI by chemoselective ligation of unprotected linear precursors," *Peptides: The Wave of the Future,* Lebl, M., et al. (Eds.), American Peptide Society, 2001, 113-114.
Botti, P., et al., "Cyclic peptides from linear unprotected peptide precursors through thiazolidine formation," *J. Am. Chem. Soc.,* 1996, 118, 10018-10024.
Byk, G., et al., "Synthesis and biological activity of NK-1 selective, N-backbone cyclic analogs of the C-terminal hexapeptide of substance P," *J. Med. Chem.,* 1996, 39 3174-3178.
Charpentier, B., et al., "Synthesis and binding affinities of cyclic and related linear analogues of $CCK_8$ selective for central receptors," *J. Med. Chem.,* 1989, 32, 1184-1190.
Chazin, W.J., et al., "Comparative studies of conformation and internal mobility in native and circular basic pancreatic trypsin inhibitor by $^1H$ nuclear magnetic resonance in solution," *Eur. J. Biochem.,* 1985, 152, 429-437.
Chu, V., et al., "Thermodynamic and structural consequences of flexible loop deletion by circular permutation in the streptavidin-biotin system," *Protein Science,* 1998, 7, 848-859.
Claeson, P., et al., "Fractionation protocol for the isolation of polypeptides from plant biomass," *J. Nat. Prod.,* 1998, 61, 77-81.
Feng, Y., et al., "Circular permutation of granulocyte colony-stimulating factor," *Biochemistry,* 1999, 38, 4553-4563.
Garrett, J.B., et al., "Are turns required for the folding of ribonuclease T1?," *Protein Science,* 1996, 5, 204-211.
Gilon, C., et al., "Backbone cyclization: a new method for conferring conformational constraint on peptides," *Biopolymers,* 1991, 31, 745-750.
Goldenberg, D.P., et al., "Circular and circularly permuted forms of bovine pancreatic trypsin inhibitor," *J. Mol. Biol.,* 1983, 165, 407-413.
Goldenberg, D.P., et al., "Folding pathway of a circular form of bovine pancreatic trysin inhibitor," *J. Mol. Biol.,* 1984, 179, 527-545.
Goldenberg, D.P., "Dissecting the roles of individual interactions in protein stability: lessons from a circularized protein," *J. Cellular Biochemistry,* 1985, 29, 321-335.
Gray, W.R., et al., "Conotoxin MI—Disulfide bonding and conformational states," *J. Biological Chemistry,* Oct. 25, 1983, 258(20), 12247-12251.
Gutknecht, R., et al., "The glucose transporter of *Escherichia coli* with circularly permuted domains is active in vivo and in vitro," *J. Biological Chemistry,* Oct. 2, 1998, 273(40), 25745-25750.
Hennecke, J., et al., "Conversion of a catalytic into a structural disulfide bond by circular permutation," *Biochemistry,* 1998, 37, 17590-17597.
Hruby, V.J., "Design of peptide hormone and neurotransmitter analogues," *TIPS,* Jun. 1985, 259-262.

(Continued)

*Primary Examiner*—Jon Weber
*Assistant Examiner*—Chih-Min Kam
(74) *Attorney, Agent, or Firm*—Woodcock Washburn LLP

(57) ABSTRACT

This invention relates to cyclized conotoxin peptides, processes for their preparation and their pharmaceutical use.

20 Claims, 3 Drawing Sheets

OTHER PUBLICATIONS

Figure 1:
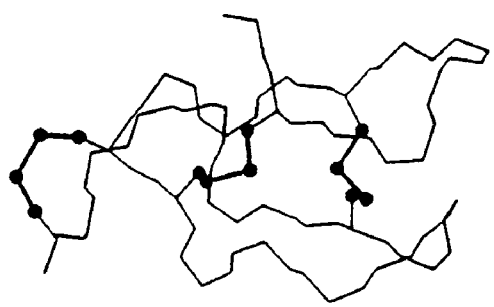
Figure 1:
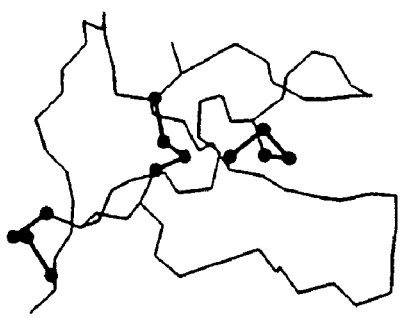
Figure 1:
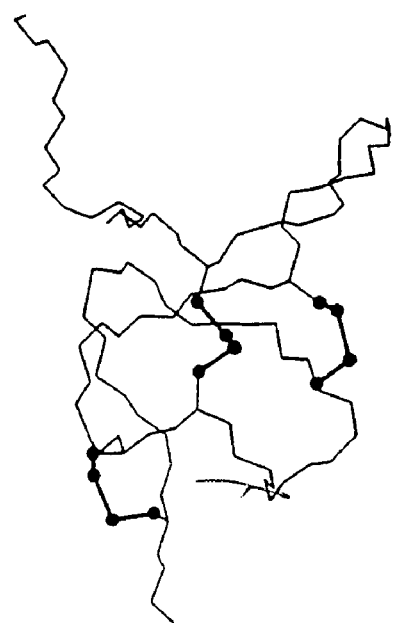

Hruby, V.J., "Conformational restrictions of biologically active peptides via amino acid side chain groups," *Life Sciences,* 1982, 31 (3), 189-199.

Jackson, D.Y., et al., "Enzymatic cyclization of linear peptide esters using subtiligase," *J. Am. Chem. Soc.,* 1995, 117, 819-820.

Jacobsen, R.B., et al., "A novel D-leucine-containing conus peptide: diverse conformational dynamics in the contryphan family," *J. Peptide Res.,* 1999, 54, 93-99.

Kreitman, R.J., "A circularly permuted recombinant interleukin 4 toxin with increased activity," *Proc. Natl. Acad. Sci. USA,* Jul. 1994, 91, 6889-6893.

Kreitman, R.J., et al., "Increased antitumor activity of a circularly permuted interleukin 4-toxin in mice with interleukin 4 receptor-bearing human carcinoma," *Cancer Research,* Aug. 1, 1995, 3357-3363.

Lender, A., et al., "Design and synthesis of sulfur-free cyclic hexapeptides which contain the RGD sequence and bind to the fibrinogen GP IIb/IIIa," *Int. J. Peptide Protein Res.,* 1993, 42, 509-517.

Muir, T.W., et al., "Expressed protein ligation: a general method for protein engineering," *Proc. Natl. Acad. Sci. USA,* Jun. 1998, 95, 6705-6710.

Myers, R.A., et al., "Conus peptides as chemical probes for receptors and ion channels," *Chem. Rev.,* 1993, 93, 1923-1936.

Okumu, F.W., et al., "Effect of restricted conformational flexibility on the permeation of model hexapeptides across caco-2 cell monolayers," *Pharmaceutical Res.,* 1997, 14(2), 169-175.

Olivera, B.M., et al., "Minireview: Conotoxins," *J. Biological Chemistry,* Nov. 25, 1991, 266(33), 22067-22070.

Olivera, B.M., "Diversity of Conus neuropeptides." *Science,* Jul. 20, 1990, 249, 257-250.

Pallaghy, P.K., et al., "A common structural motif incorporating a cystine knot and a triple-stranded β-sheet in toxic and inhibitory polypeptides," *Protein Science,* 1994, 3, 1833-1839.

Rivier, J. E., et al., "Bicyclic gonadotropin releasing hormone (GnRH) antagonists," *Peptides Chemistry, Structure and Biology,* 1990, 33-37.

Rote, K. V., et al., "Circular pancreatic trypsin inhibitor: A novel substrate for studies on intracellular proteolysis," *J. Biological Chemistry,* Jan. 15, 1989, 264(2), 1156-1162.

Saether, O., et al., "Elucidation of the primary and three-dimensional structure of the uterotonic polypeptide kalata B1," *Biochemistry,* 1995, 34, 4147-4158.

Tam, J.P., et al., "Thia zip reaction for synthesis of large cyclic peptides: mechanisms and applications," *J. Am. Chem. Soc.,* 1999, 121, 4316-4324.

Tam, J.P., et al., "Synthesis of large cyclic cystine-knot peptide by orthogonal coupling strategy using unprotected peptide precursor," *Tetrahedron Letters,* 1997, 38(32), 5599-5602.

Tam, J.P., "A biomimetic strategy in the synthesis and fragmentation of cyclic protein," *Protein Science,* 1998, 7, 1583-1592.

Terada, S., et al., "Synthesis and hydrolysis by pepsin and trypsin of a cyclic hexapeptide containing lysine and phenylalanine," *Eur. J. Biochem.,* 1975, 52, 273-282.

Wieligmann, K., et al., "Eye lens βB2-crystallin: circular permutation does not influence the oligomerization state but enhances the conformational stability." *J. Mol. Biol.,* 1998, 280, 721-729.

Zhang, L., et al., "Synthesis and application of unprotected cyclic peptides as building blocks for peptide dendrimers." *J. Am. Chem. Soc.,* 1997, 119. 2363-2370.

* cited by examiner

```
                            SEQUENCE LISTING

<160> NUMBER OF SEQ ID NOS: 29

<210> SEQ ID NO 1
<211> LENGTH: 7
<212> TYPE: PRT
<213> ORGANISM: Artificial
<220> FEATURE:
<223> OTHER INFORMATION: Synthetic Construct

<400> SEQUENCE: 1

Thr Arg Asn Gly Leu Pro Gly
1               5

<210> SEQ ID NO 2
<211> LENGTH: 4
<212> TYPE: PRT
<213> ORGANISM: Artificial
<220> FEATURE:
<223> OTHER INFORMATION: Synthetic Construct

<400> SEQUENCE: 2

Thr Arg Asn Gly
1

<210> SEQ ID NO 3
<211> LENGTH: 7
<212> TYPE: PRT
<213> ORGANISM: Artificial
<220> FEATURE:
<223> OTHER INFORMATION: Synthetic Construct

<400> SEQUENCE: 3

Thr Arg Gly Gly Leu Pro Val
1               5

<210> SEQ ID NO 4
<211> LENGTH: 3
<212> TYPE: PRT
<213> ORGANISM: Artificial
<220> FEATURE:
<223> OTHER INFORMATION: Synthetic Construct

<400> SEQUENCE: 4

Thr Asn Gly
1

<210> SEQ ID NO 5
<211> LENGTH: 32
<212> TYPE: PRT
<213> ORGANISM: Artificial
<220> FEATURE:
<223> OTHER INFORMATION: cyclic conotoxin peptide
```

<400> SEQUENCE: 5

Cys Lys Gly Lys Gly Ala Lys Cys Ser Arg Leu Met Tyr Asp Cys Cys
1               5                   10                  15

Thr Gly Ser Cys Arg Ser Gly Lys Cys Thr Arg Asn Gly Leu Pro Gly
            20                  25                  30

<210> SEQ ID NO 6
<211> LENGTH: 29
<212> TYPE: PRT
<213> ORGANISM: Artificial
<220> FEATURE:
<223> OTHER INFORMATION: cyclic conotoxin peptide

<400> SEQUENCE: 6

Cys Lys Gly Lys Gly Ala Lys Cys Ser Arg Leu Met Tyr Asp Cys Cys
1               5                   10                  15

Thr Gly Ser Cys Arg Ser Gly Lys Cys Thr Arg Asn Gly
            20                  25

<210> SEQ ID NO 7
<211> LENGTH: 32
<212> TYPE: PRT
<213> ORGANISM: Artificial
<220> FEATURE:
<223> OTHER INFORMATION: cyclic conotoxin peptide

<400> SEQUENCE: 7

Gly Leu Pro Val Cys Lys Gly Lys Gly Ala Lys Cys Ser Arg Leu Met
1               5                   10                  15

Tyr Asp Cys Cys Thr Gly Ser Cys Arg Ser Gly Lys Cys Thr Arg Gly
            20                  25                  30

<210> SEQ ID NO 8
<211> LENGTH: 19
<212> TYPE: PRT
<213> ORGANISM: Artificial
<220> FEATURE:
<223> OTHER INFORMATION: cyclic conotoxin peptide

<400> SEQUENCE: 8

Gly Cys Cys Ser Asn Pro Val Cys His Leu Glu His Ser Asn Leu Cys
1               5                   10                  15

Thr Asn Gly

<210> SEQ ID NO 9
<211> LENGTH: 19
<212> TYPE: PRT
<213> ORGANISM: Artificial
<220> FEATURE:
<223> OTHER INFORMATION: cyclic conotoxin peptide

<400> SEQUENCE: 9

Cys Cys Ser Asn Pro Val Cys His Leu Glu His Ser Asn Leu Cys Thr
1               5                   10                  15

Asn Gly Gly

<210> SEQ ID NO 10
<211> LENGTH: 25
<212> TYPE: PRT
<213> ORGANISM: Conus magus

<400> SEQUENCE: 10

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 11
<211> LENGTH: 25
<212> TYPE: PRT
<213> ORGANISM: Conus magus
<220> FEATURE:
<221> NAME/KEY: MISC_FEATURE
<222> LOCATION: (7)..(7)
<223> OTHER INFORMATION: X = 4-hydroxyproline

<400> SEQUENCE: 11

Cys Lys Gly Lys Gly Ala Xaa Cys Ser Arg Leu Met Tyr Asp Cys Cys
1               5                   10                  15

Thr Gly Ser Cys Arg Ser Gly Lys Cys
            20                  25

<210> SEQ ID NO 12
<211> LENGTH: 27
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: X = 4-hydroxyproline
<220> FEATURE:
<221> NAME/KEY: MISC_FEATURE
<222> LOCATION: (10)..(10)
<223> OTHER INFORMATION: X = 4-hydroxyproline
<220> FEATURE:
<221> NAME/KEY: MISC_FEATURE
<222> LOCATION: (21)..(21)
<223> OTHER INFORMATION: X = 4-hydroxyproline

<400> SEQUENCE: 12

Cys Lys Ser Xaa Gly Ser Ser Cys Ser Xaa Thr Ser Tyr Asn Cys Cys
1               5                   10                  15

Arg Ser Cys Asn Xaa Tyr Thr Lys Arg Cys Tyr
            20                  25

<210> SEQ ID NO 13
<211> LENGTH: 24
<212> TYPE: PRT
<213> ORGANISM: Conus striatus
<220> FEATURE:
<221> NAME/KEY: MISC_FEATURE
<222> LOCATION: (7)..(7)
<223> OTHER INFORMATION: X = 4-hydroxyproline

<400> SEQUENCE: 13

Cys Arg Ser Ser Gly Ser Xaa Cys Gly Val Thr Ser Ile Cys Cys Gly
1               5                   10                  15

Arg Cys Tyr Arg Gly Lys Cys Thr
            20

<210> SEQ ID NO 14
<211> LENGTH: 26
<212> TYPE: PRT
<213> ORGANISM: Conus striatus

<400> SEQUENCE: 14

Cys Lys Leu Lys Gly Gln Ser Cys Arg Lys Thr Ser Tyr Asp Cys Cys
1               5                   10                  15

Ser Gly Ser Cys Gly Arg Ser Gly Lys Cys
            20                  25

<210> SEQ ID NO 15
<211> LENGTH: 29
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: X = 4-hydroxyproline
<220> FEATURE:
<221> NAME/KEY: MISC_FEATURE
<222> LOCATION: (7)..(7)
<223> OTHER INFORMATION: X = 4-hydroxyproline

<400> SEQUENCE: 15

Cys Lys Ser Xaa Gly Thr Xaa Cys Ser Arg Gly Met Arg Asp Cys Cys
1               5                   10                  15

Thr Ser Cys Leu Leu Tyr Ser Asn Lys Cys Arg Arg Tyr
            20                  25

<210> SEQ ID NO 16
<211> LENGTH: 29
<212> TYPE: PRT
<213> ORGANISM: Conus geographus
<220> FEATURE:
<221> NAME/KEY: MISC_FEATURE
<222> LOCATION: (4)..(4)
<223> OTHER INFORMATION: X = 4-hydroxyproline
<220> FEATURE:
<221> NAME/KEY: MISC_FEATURE
<222> LOCATION: (7)..(7)
<223> OTHER INFORMATION: X = 4-hydroxyproline

<400> SEQUENCE: 16

Cys Lys Ser Xaa Gly Thr Xaa Cys Ser Arg Gly Met Arg Asp Cys Cys
1               5                   10                  15

Thr Ser Cys Leu Ser Tyr Ser Asn Lys Cys Arg Arg Tyr
            20                  25

<210> SEQ ID NO 17
<211> LENGTH: 27
<212> TYPE: PRT
<213> ORGANISM: Conus tulipa
<220> FEATURE:
<221> NAME/KEY: MISC_FEATURE
<222> LOCATION: (4)..(4)
<223> OTHER INFORMATION: X = 4-hydroxyproline
<220> FEATURE:
<221> NAME/KEY: MISC_FEATURE
<222> LOCATION: (10)..(10)
<223> OTHER INFORMATION: X = 4-hydroxyproline
<220> FEATURE:
<221> NAME/KEY: MISC_FEATURE
<222> LOCATION: (21)..(21)
<223> OTHER INFORMATION: X = 4-hydroxyproline

<400> SEQUENCE: 17

Cys Leu Ser Xaa Gly Ser Ser Cys Ser Xaa Thr Ser Tyr Asn Cys Cys
1               5                   10                  15

Arg Ser Cys Asn Xaa Tyr Ser Arg Lys Cys Arg
            20                  25

<210> SEQ ID NO 18
<211> LENGTH: 27
<212> TYPE: PRT
<213> ORGANISM: Conus purpurascens
<220> FEATURE:

```
<221> NAME/KEY: MISC_FEATURE
<222> LOCATION: (4)..(4)
<223> OTHER INFORMATION: X = 4-hydroxyproline

<400> SEQUENCE: 18

Cys Arg Ile Xaa Asn Gln Lys Cys Phe Gln His Leu Asp Asp Cys Cys
1               5                   10                  15

Ser Arg Lys Cys Asn Arg Phe Asn Lys Cys Val
            20                  25

<210> SEQ ID NO 19
<211> LENGTH: 13
<212> TYPE: PRT
<213> ORGANISM: Conus geographus

<400> SEQUENCE: 19

Glu Cys Cys Asn Pro Ala Cys Gly Arg His Tyr Ser Cys
1               5                   10

<210> SEQ ID NO 20
<211> LENGTH: 12
<212> TYPE: PRT
<213> ORGANISM: Conus imperialis

<400> SEQUENCE: 20

Gly Cys Cys Ser Asp Pro Arg Cys Ala Trp Arg Cys
1               5                   10

<210> SEQ ID NO 21
<211> LENGTH: 15
<212> TYPE: PRT
<213> ORGANISM: Conus pennaceus

<400> SEQUENCE: 21

Gly Cys Cys Ser Pro Pro Cys Ala Ala Asn Asn Pro Asp Tyr Cys
1               5                   10                  15

<210> SEQ ID NO 22
<211> LENGTH: 16
<212> TYPE: PRT
<213> ORGANISM: Conus pennaceus

<400> SEQUENCE: 22

Gly Cys Cys Ser Leu Pro Pro Cys Ala Leu Ser Asn Pro Asp Tyr Cys
1               5                   10                  15

<210> SEQ ID NO 23
<211> LENGTH: 19
<212> TYPE: PRT
<213> ORGANISM: Conus striatus

<400> SEQUENCE: 23

Gly Cys Cys Cys Asn Pro Ala Cys Gly Pro Asn Tyr Gly Cys Gly Thr
1               5                   10                  15

Ser Cys Ser

<210> SEQ ID NO 24
<211> LENGTH: 16
<212> TYPE: PRT
<213> ORGANISM: Conus magus

<400> SEQUENCE: 24

Gly Cys Cys Ser Asn Pro Asx Cys His Leu Glu His Ser Asn Leu Cys
1               5                   10                  15
```

```
<210> SEQ ID NO 25
<211> LENGTH: 22
<212> TYPE: PRT
<213> ORGANISM: Conus geographus
<220> FEATURE:
<221> NAME/KEY: MISC_FEATURE
<222> LOCATION: (6)..(7)
<223> OTHER INFORMATION: X = 4-hydroxyproline
<220> FEATURE:
<221> NAME/KEY: MISC_FEATURE
<222> LOCATION: (17)..(17)
<223> OTHER INFORMATION: X = 4-hydroxyproline

<400> SEQUENCE: 25

Arg Asp Cys Cys Thr Xaa Xaa Lys Lys Cys Lys Asp Arg Gln Cys Lys
1               5                   10                  15

Xaa Gln Arg Cys Cys Ala
            20

<210> SEQ ID NO 26
<211> LENGTH: 22
<212> TYPE: PRT
<213> ORGANISM: Conus geographus
<220> FEATURE:
<221> NAME/KEY: MISC_FEATURE
<222> LOCATION: (6)..(7)
<223> OTHER INFORMATION: X = 4-hydroxyproline
<220> FEATURE:
<221> NAME/KEY: MISC_FEATURE
<222> LOCATION: (17)..(17)
<223> OTHER INFORMATION: X = 4-hydroxyproline

<400> SEQUENCE: 26

Arg Asp Cys Cys Thr Xaa Xaa Arg Lys Cys Lys Asp Arg Arg Cys Lys
1               5                   10                  15

Xaa Met Lys Cys Cys Ala
            20

<210> SEQ ID NO 27
<211> LENGTH: 22
<212> TYPE: PRT
<213> ORGANISM: Conus geographus
<220> FEATURE:
<221> NAME/KEY: MISC_FEATURE
<222> LOCATION: (6)..(7)
<223> OTHER INFORMATION: X = 4-hydroxyproline
<220> FEATURE:
<221> NAME/KEY: MISC_FEATURE
<222> LOCATION: (17)..(17)
<223> OTHER INFORMATION: X = 4-hydroxyproline

<400> SEQUENCE: 27

Arg Asp Cys Cys Thr Xaa Xaa Lys Lys Cys Lys Asp Arg Arg Cys Lys
1               5                   10                  15

Xaa Leu Lys Cys Cys Ala
            20

<210> SEQ ID NO 28
<211> LENGTH: 22
<212> TYPE: PRT
<213> ORGANISM: Conus purpurascens
<220> FEATURE:
<221> NAME/KEY: MISC_FEATURE
<222> LOCATION: (8)..(8)
<223> OTHER INFORMATION: X = 4-hydroxyproline
<220> FEATURE:
<221> NAME/KEY: MISC_FEATURE
<222> LOCATION: (18)..(18)
```

```
<223> OTHER INFORMATION: X = 4-hydroxyproline

<400> SEQUENCE: 28

Glx Arg Leu Cys Cys Gly Phe Xaa Lys Ser Cys Arg Ser Arg Gln Cys
1               5                   10                  15

Lys Xaa His Arg Cys Cys
            20

<210> SEQ ID NO 29
<211> LENGTH: 33
<212> TYPE: PRT
<213> ORGANISM: Conus geographus

<400> SEQUENCE: 29

Ala Cys Ser Arg Gly Ser Arg Cys Pro Pro Gln Cys Cys Met Gly Leu
1               5                   10                  15

Arg Cys Gly Arg Gly Asn Pro Gln Lys Cys Ile Gly Ala His Glu Asp
            20                  25                  30

Val
```

CYCLIZED CONOTOXIN PEPTIDES

This application is a 371 of PCT/AU99/00769, filed Sep. 14, 1999, which claims the foreign priority of Australia Application PP5895, filed Sep. 14, 1998.

This invention relates to novel peptides and derivatives thereof, in particular to a range of cyclic peptides useful in the therapeutic treatment of humans. The invention also relates to pharmaceutical compositions comprising these peptides, methods for making the peptides and the use of these peptides in the prophylaxis or treatment of conditions or diseases in humans.

The marine nails of the genus *Conus* (cone snails) use a sophisticated biochemical strategy to capture their prey. As predators of either fish, worms or other molluscs, the cone snails inject their prey with venom containing a cocktail of small bioactive peptides. These toxin molecules, which are referred to as conotoxins, interfere with neurotransmission by targeting a variety of receptors and ion-channels. They typically contain 12–30 amino acids arranged in linear sequence. The venom from any single *Conus* species may contain more than 100 different peptides. The conotoxins are divided into classes on the basis of their physiological targets. To date, ten classes have been described. The ω-conotoxin class of peptides target and block voltage-sensitive $Ca^{2+}$-channels inhibiting neurotransmitter release. The α-conotoxins and ψ-conotoxins target and block nicotinic ACh receptors, causing ganglionic and neuromuscular blockade. Peptides of the μ-conotoxin class act on voltage-sensitive $Na^+$-channels and block muscle and nerve action potentials. The δ-conotoxins target and delay the inactivation of voltage-sensitive $Na^+$-channels enhancing neuronal excitability. The κ-conotoxin class of peptides target and block voltage-sensitive $K^+$-channels, and these may also cause enhanced neuronal excitability. The conopressins are vasopressin receptor antagonists and the conantokins are NMDA receptor antagonists. Recently, the prototype of a new γ-conotoxin class was described, which targets a voltage-sensitive nonspecific cation channel, and of a new σ-conotoxin class, which antagonises the $5HT_3$ receptor.

Most conotoxin peptides contain either four (4) or six (6) cysteine residues which are bonded in pairs to form either two (2) or three (3) disulfide bonds respectively. As indicated above they bind to a range of different ion-channels in mammals, and accordingly they have several potential therapeutic applications, including pain relief and neuroprotection in humans. However, in general peptides have several difficulties associated with their use as drugs, including generally poor bioavailability, susceptibility to cleavage by proteases, and unwanted side effects.

One conotoxin, MVIIA, is currently in clinical trial for the treatment of intractable pain and for neuroprotection following stroke. In the former indication the route of administration is restricted to intrathecal infusion into the spinal cord because of some of the above-mentioned difficulties.

The present invention is based on the finding that cyclisation of the peptide backbone of conotoxins to produce non-natural analogues results in new molecules which can retain the therapeutic activity of the non-cyclised peptide.

Accordingly in a first aspect the present invention provides a cyclised conotoxin peptide.

These cyclised conotoxins have improved properties relative to their "linear" conotoxin counterparts. The improved properties may include the following:
1. Resistance to cleavage by proteases.
2. High chemical stability.
3. An additional "handle" on the molecule which does not interfere with the primary biological effect of the conotoxin, but provides a place for functionalising the molecule to improve biophysical properties or, in some cases, reduce side effects.
4. Improved bioavailability.

The conotoxin peptide may be any conotoxin peptide which is capable of being cyclised. It may be a naturally occurring conotoxin peptide, or a derivative thereof. Preferably the conotoxin peptide is one which, in its non-cyclised form, has an activity associated with the therapeutic treatment of mammals, such as humans. Since the cyclisation of the peptide has the potential to alter the activity of the peptide, or introduce new activities, it is possible that some cyclised conotoxin peptides may have improved therapeutic properties relative to "linear" conotoxins.

Examples of suitable linear naturally occurring conotoxins and derivatives thereof which may be cyclised according to the present invention include those described in Olivera, B. M. et al., 1991; Myers, R. A. et al., 1993; Hopkins, C. et al., 1995; Olivera, B. M. et al., 1990. Preferably the conotoxins are selected from the ω-class, which have characteristic three disulphide bonds forming a "cystine knot", although other classes of conotoxins may also be cyclised.

Examples of suitable naturally occurring ω-conotoxin peptides include MVIIA, GVIA, SVIB, SVIA, TVIA, MVIIC, GVIIA and GVIIB.

The conotoxin peptides have a characteristic folding pattern which is based on the number of disulphide bonds, and the location on the peptide of the cysteine residues which participate in the disulphide bonding pattern. Where there are three disulphide bonds there is the potential for the peptide to form a cystine knot. A cystine knot occurs when a disulphide bond passes through a closed cyclic loop formed by two disulphide bonds and amino acids in the peptide chain. The cyclisation of a conotoxin having a cystine knot produces a particularly stable peptide structure. As well as being present in the class of omega-conotoxins, Nielson, et al., 1996, the cystine knot exists in other classes including, $K^+$ channel blockers (eg conotoxin PVIIA; Scanlon et al., 1997) and Na channel blockers (eg conotoxin GS; Hill et al., 1997).

Preferred conotoxin peptides are those in which, in their folded form, have N- and C-termini which are located in close proximity. The proximity of termini is illustrated above for MVIIA and PVIIA. In conotoxin GS the N and C termini are further apart, but the C terminus contains a flexible tail which can readily alter conformation to approach the N terminus.

The cyclic conotoxin peptides according to the present invention will generally consist of a conotoxin peptide in which the N- and C-termini are linked via a linking moiety, although in some cases it may be possible to directly connect the N- and C-termini of a naturally occurring conotoxin peptide or derivative thereof without the need for a linking moiety. The linking moiety, if present, may be a peptide linker such that cyclisation produces an amide-cyclised peptide backbone. These peptides will have no free N- or C-termini.

Accordingly in this aspect of the present invention there is provided a cyclised conotoxin peptide comprising a linear conotoxin peptide and a peptide linker, wherein the N- and C-termini of the linear peptide are linked via the peptide linker to form an amide cyclised peptide backbone.

No examples of cyclic conotoxins have been previously described in the literature, but it is in principle possible to make molecules which have a cyclic backbone, part of which incorporates the natural sequence and disulfide bond connections of linear conotoxins.

Cyclisation may also be achieved using other linking moieties, such as those including organic linkers, non-native peptide bonds such as thio-ether linkages and side-chain to N or C-termini cyclisation.

Considerable variation in the peptide sequence of the linking moiety is possible. Since this linking region does not bind to the primary active site of the conotoxin it can be modified to alter physiochemical properties, and potentially reduce side effects of the conotoxins.

In linking the N- and C-termini of the conotoxin it may in some cases be necessary or desirable to remove one or more of the N- or C-termini residues. Such modification of the linear conotoxin sequence is within the scope of the present invention.

The linking moiety will necessarily be of sufficient length to span the distance between the N- and C-termini of the conotoxin peptide. In the case of peptide linkers the length will generally be in the order of 2 to 15 amino acids. In some cases longer or shorter peptide linkers may be required.

Examples of possible peptide linkers include:

```
TRNGLPG      SEQ ID NO. 1
TRNG         SEQ ID NO. 2
TRGGLPV      SEQ ID NO. 3
TNG          SEQ ID NO. 4
```

It is possible, according to the present invention, to modify or potentiate the activity of a conotoxin peptide by selection of a particular size and/or type of peptide linker. Small changes in the conformation of the conotoxin caused by the introduction of a linking group can alter the binding affinities of the peptides for their particular binding sites. Conversely, where the activity is to be as close to the activity of the parent conotoxin peptide as possible, a linker will be selected which minimises any change in conformation.

There are several ways in which cyclic conotoxins may be synthesised. These include the following:

1. Cyclisation of the Reduced Peptide Followed by Oxidation to Form the Required Disulfide Bonds.

Figure 2:
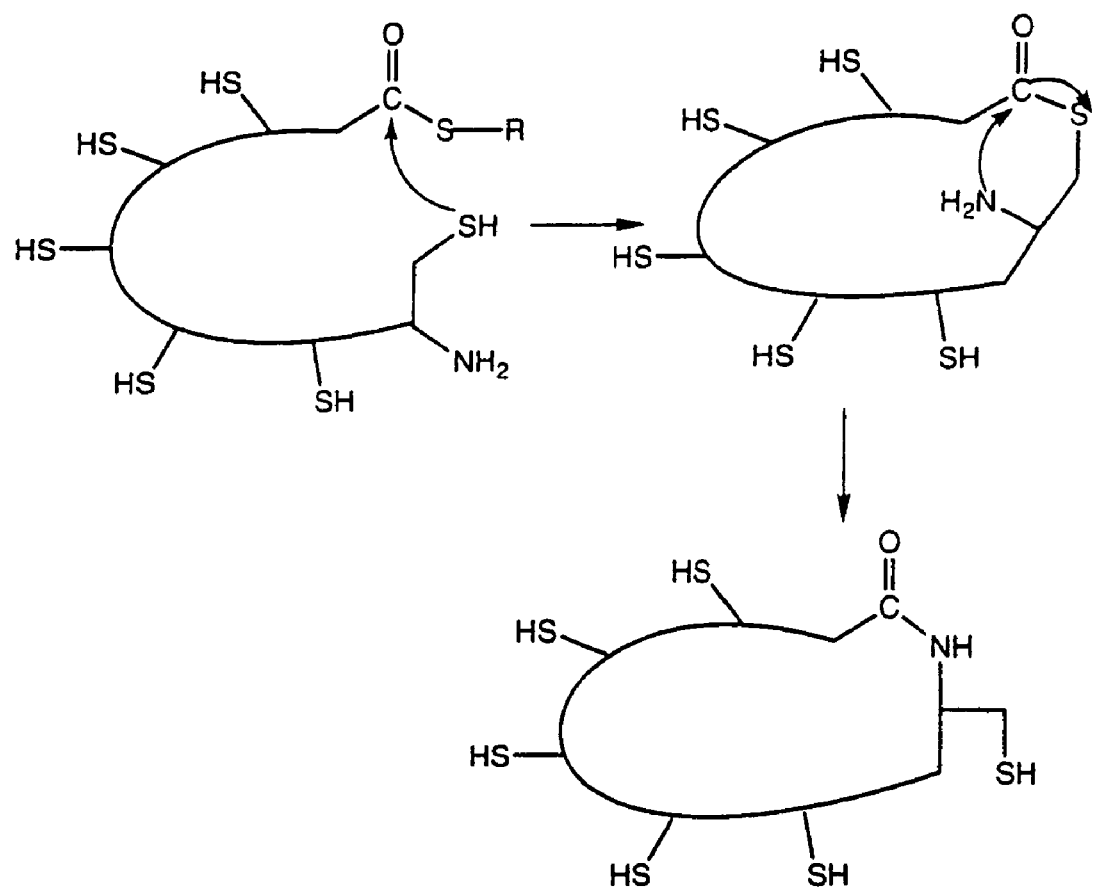

In this approach an extended linear peptide is first synthesised "on resin" using solid phase peptide synthesis methods. This extended linear peptide comprises the native sequence starting at a cysteine residue at, or closest to, the N-terminus and a C-terminal extension which comprises the new linking moiety. The solid phase synthesis actually starts in the reverse order—ie at the C-terminus of the extended linear peptide. Following cleavage from the resin, the extended conotoxin is cyclised to a thioester intermediate which subsequently rearranges to an amide-cyclised peptide. This reduced peptide is then oxidised to form the disulfide bonds. A schematic diagram of the reaction involved in the cyclisation is shown in FIG. 2. The linear peptide is cleaved from the resin with the linker to the resin (R) still attached. R corresponds to the linker between the peptide and the resin and is different from the linking moiety used in the cyclisation. The first reaction involves the formation of a thioester between the thiol of the N-terminal cysteine and the carboxy terminus. This then undergoes an S, N acyl migration to form the cyclic peptide with a native peptide bond.

2. Oxidation of the Reduced Linear Peptide, Followed by Cyclisation.

In this approach an extended peptide is assembled using solid phase peptide synthesis. The extended linear peptide comprises the native conotoxin sequence with extra residues added at the N- and/or C-termini. The N and C termini should preferably be glycine residues. The peptide is folded, and in the case of the conotoxin-like peptides, the termini of the folded molecule are generally close together in space. This facilitates the cyclisation of the peptide in solution using standard chemistry. Complications may occur when large numbers of lysine, glutamic acid or aspartic acid residues are present in the sequence and method 1 is then preferable.

3. Ligation of a Linker onto an Existing Conotoxin, Followed by Cyclisation.

In this method the starting material is a mature conotoxin. A peptide linker is synthesised and ligated with the conotoxin using published procedures for the ligation of peptides. The extended peptide is then cyclised and oxidised.

Accordingly in a further aspect of the invention there is provided a process for preparing a cyclic conotoxin comprising:

A
  (i) synthesising an extended linear conotoxin peptide on a solid phase support, said extended linear conotoxin peptide comprising a linear conotoxin peptide having a linker moiety attached to at least one end thereof,
  (ii) cleaving said extended linear peptide from the support
  (iii) cyclising said extended linear conotoxin peptide, and
  (iv) oxidising said cyclised peptide to form disulphide bonds, or B
  (i) synthesising an extended linear conotoxin peptide on a solid phase support, said extended linear conotoxin peptide comprising a linear conotoxin peptide having a linker moiety attached to at least one end thereof,
  (ii) cleaving said extended linear peptide from the solid support
  (iii) subjecting said extended peptide to conditions such that the peptide folds and forms the required disulphide bonds, and
  (iv) cyclising the folded peptide, or C
  (i) reacting a conotoxin peptide with a linker moiety to form an extended linear conotoxin peptide having said linker moiety attached to one end thereof, and
  (ii) cyclising said extended peptide and oxidising to form disulphide bonds, if required.

In the process described above the steps can be performed in any order, provided the product is a cyclic conotoxin having the required disulphide bonds. For example, in process A the cleavage and cyclisation steps may be performed simultaneously or in either order. Similarly in process B the cyclisation and folding steps could be performed simultaneously, or in either order.

It is also possible to form the disulphide bonds selectively using protecting groups on the cysteine residues. Selective protection of the cysteine residues in this way allows the production of a particular disulphide bond pattern. Examples of groups capable of protecting cysteine residues include acetamidomethyl (Acm), 4-methylbenzyl (MeBzl) and 4-methoxybenzyl (Mob).

Also, in view of the cyclic nature of the final products, synthetic procedures may involve cyclic permutation of the above procedures. For example, the designs of the extended linear peptide for α-conotoxins could commence by adding a linker to the C-terminal residue of the α-conotoxin, cyclically permuting the N-terminal residue(s) to the C-terminal, to provide an N-terminal cysteine, and cyclising as described. Some examples of linear conotoxins which are currently known and to which the cyclisation approach can be applied are listed in Table 1.

Additions encompass the addition of one or more naturally occurring or non-conventional amino acid residues. Deletion encompasses the deletion of one or more amino acid residues.

| Conotoxin | Sequence | |
|---|---|---|
| Omega conotoxins | | |
| MVIIA | CKGKGAKCSRLMYDCCTGSCRS--GKC | (SEQ ID NO:10) |
| MVIIC | CKGKGAOCRKTMYDCCSGSCGRR--GKC | (SEQ ID NO:11) |
| GVIA | CKSOGSSCSOTSYNCCR-SCNOYTKRCY | (SEQ ID NO.12) |
| SVIA | CRSSGSOCGVTSI-CCGR-CYR--GKCT | (SEQ ID NO:13) |
| SVIB | CKLKGQSCRKTSYDCCSGSCGRS-GKC | (SEQ ID NO:14) |
| GVIIA | CKSOGTOCSRGMRDCCTS-CLLYSNKCRRY | (SEQ ID NO:15) |
| GVIIB | CKSOGTOCSRGMRDCCTS-CLSYSNKCRRY | (SEQ ID NO:16) |
| TVIA | CLSOGSSCSOTSYNCCRS-CNOYSRKCR | (SEQ ID NO:17) |
| Kappa conotoxin | | |
| PVIIA | CRIONQKCFQHLDDCCSRKCNRFNKCV | (SEQ ID NO:18) |
| Alpha conotoxins | | |
| GI | ECCNPA-CGRHYS--C | (SEQ ID NO:19) |
| IMI | GCCSDPRCAWR----C | (SEQ ID NO:20) |
| PNIA | GCCSLPPCAANNPDYC | (SEQ ID NO:21) |
| PNIB | GCCSLPPCALSNPDYC | (SEQ ID NO:22) |
| SII | GCCCNPACGPNYG--CGTSCS | (SEQ ID NO:23) |
| MII | GCCSNPBCHLEHSNLC | (SEQ ID NO:24) |
| Mu conotoxin | | |
| GIIIA | -RDCCTOOKKCKDRQCKOQRCCA | (SEQ ID NO:25) |
| GIIIB | -RDCCTOORKCKDRRCKOMKCCA | (SEQ ID NO:26) |
| GIIIC | -RDCCTOOKKCKDRRCKOLKCCA | (SEQ ID NO:27) |
| PIIIA | ZRLCCGFOKSCRSRQCKOHRCC | (SEQ ID NO:28) |
| GS | ACSGRGSRCPPQCCMGLRCGRGNPQKCIGAHEDV | (SEQ ID NO:29) |

The term "derivative" as used herein in connection with naturally occurring conotoxin peptides, such as MVIIA, refers to a peptide which differs from the naturally occurring peptides by one or more amino acid deletions, additions, substitutions, or side-chain modifications.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality, or size, for example Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some non-conventional amino acids may also be suitable replacements for the naturally occurring amino acids. For example ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as a naturally-occurring amino acid from a different group (eg. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Preferably, amino acid substitutions are conservative.

As stated above the present invention includes peptides in which one or more of the amino acids has undergone sidechain modifications. Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

A list of some amino acids having modified side chains and other unnatural amino acids is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |

TABLE 2-continued

| Non-conventional amino acid | Code | Non-conventional amino acid | Code |
| --- | --- | --- | --- |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2.2-diphenyl-ethylamino)cyclopropane | Nmbc | L-O-methyl-serine | Omser |
|  |  | L-O-methyl homoserine | Omhser |

These types of modifications may be important to stabilise the peptide if administered to an individual or for use as a diagnostic reagent.

Other derivatives contemplated by the present invention include a range of glycosylation variants from a completely unglycosylatecd molecule to a modified glycosylated molecule. Altered glycosylation patterns may result from expression of recombinant molecules in different host cells.

Preferably cyclic conotoxin peptides will retain the Cys residues and characteristic disulphide bonding pattern. Derivatives may include additional Cys residues provided they are protected during formation of the disulphide bonds.

Preferably the conotoxin peptides according to the invention have 12 to 40 amino acids, more preferably 15 to 30.

Naturally occurring conotoxins are widely used as neuropharmacological probes. They bind very tightly and highly selectivity to ion channel receptors. In these applications they are incubated with a relevant tissue preparation and their binding, or biological effects are measured. Their actions will be reduced or destroyed if they are metabolized by endogenous enzymes. Optimum performance of pharmacological probes thus requires resistance to enzymatic or chemical breakdown. Since the cyclic conotoxin peptides possess the desirable properties described above they may be better pharmacological probes than naturally occurring conotoxin peptides in some cases.

Still another aspect of the present invention is directed to antibodies to the cyclic peptides according to the invention. Such antibodies may be monoclonal or polyclonal and may be selected from naturally occurring antibodies to the peptides or may be specifically raised to the peptides using standard techniques. In the case of the latter, the peptides may first need to be associated with a carrier molecule. The antibodies of the present invention are particularly useful as therapeutic or diagnostic agents.

In this regard, specific antibodies can be used to screen for the peptides according to the invention. Techniques for such assays are well known in the art and include, for example, sandwich assays and ELISA. Knowledge of peptide levels may be important for monitoring certain therapeutic protocols.

The cyclic conotoxin peptides according to the present invention are useful as therapeutic agents.

Accordingly the present invention provides a method for the treatment or prophylaxis of conditions or diseases in mammals, preferably humans, including the step of administering a cyclic conotoxin peptide.

In particular omega-conotoxins which block N-type calcium channels may be useful in the treatment of neurological disorders such as acute and chronic pain, stroke, traumatic brain injury, migraine, epilepsy, Parkinson's disease, Alzheimer's disease, multiple schlerosis, and depression. The α-conotoxins bind to nicotinic acetylcholine receptors (nAChRs). Such receptors have been implicated in the pathophysiology of several neuropsychiatric disorders including schizophrenia, Alzheimer's disease, Parkinson's disease and Tourette's syndrome and thus the α-conotoxins have potential therapeutic indications for these diseases. The μ-conotoxins target sodium channels. Those μ-conotoxins that interact with neuronal channels (eg PIIIA) have potential therapeutical applications in the treatment of chronic and neuropathic pain.

Assays useful for assessing compounds with the above mentioned activities may be in vitro or in vivo and are known to those skilled in the art. For example, assays useful for assessing activity at N-type calcium channels include those described or referenced in WO91/07980, WO93/13128, U.S. Pat. No. 5,824,645, WO97/04797, Drugs of the Future (1994 and 1998), Drug Data Report (1993), or Heading (1999). The cyclic peptides according to the invention, or labelled derivatives thereof, may also be useful in such assays.

Preferably the mammal is in need of such treatment although the peptide may be administered in a prophylactic sense.

The invention also provides a composition comprising a cyclic conotoxin peptide, and a pharmaceutically acceptable carrier or diluent.

Preferably the composition is in the form of a pharmaceutical composition.

There is also provided the use of a cyclic conotoxin peptide in the manufacture of a medicament for the treatment or prophylaxis of diseases or conditions of mammals, preferably of humans.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action. In view of the improved stability of the cyclic peptides relative to their "linear" counterparts a wider range of formulation types and routes of administration is available. Known conotoxins can generally only be administered successfully intrathecally which means that the patient must be hospitalised. Administration of the cyclic peptides according to the present invention is not subject to the same restriction.

The pharmaceutical forms suitable for injectable use include sterile injectable solutions or dispersions, and sterile powders for the extemporaneous preparation of sterile injectable solutions. They should be stable under the conditions of manufacture and storage and may be preserved against the contaminating action of microorganisms such as bacteria or fungi. The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal injection or infusion.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected it may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example topical application such as creams, lotions and gels, or compositions suitable for inhalation or intranasal delivery, for example solutions or dry powders.

Parenteral dosage forms are preferred, including those suitable for intravenous, intrathecal, or intracerebral delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 µg to about 2000 mg. Expressed in proportions, the active compound is generally present in from about 0.25 µg to about 2000 mg/ml of carrier. In the case of compositions containing supplementary active ingredients, the dosages are determined by reference to the usual dose and manner of administration of the said ingredients.

The invention will now be described with reference to the accompanying examples and figures which describe the production of some cyclic conotoxin peptides and their biological activity and illustrate the structures of some linear conotoxin peptides which may be subjected to cyclisation. However, it is to be understood that the particularity of the following description is not to supersede the generality of the preceding description of the invention.

Referring to the figures:

FIG. 1 is a representation of the three-dimensional structures of the conotoxins PVIIA, MVIIA and GS. The structures were determined by NMR spectroscopy. The backbone atoms are displayed as lines and the disulfide bonds are highlighted as balls and sticks. All three conotoxins, although from different classes and hence having different activities, have similar structures which contain a cystine knot motif.

FIG. 2 is a scheme for peptide cyclisation via a C-terminal thioester. The free sulfur of an N-terminal cysteine interacts with the C-terminal thioester to form an intermediate which undergoes an S, N, acyl migration to form a cyclic peptide with a native peptide bond.

FIG. 3 is a representation of the three-dimensional structures of the conotoxins PVIIA, MVIIA, SVIB, GI and IMI. The structures were determined by NMR spectroscopy. The backbone atoms are shown as lines and the N- and C-termini are connected by a dotted line which has the intervening distance shown above. The α-conotoxins, GI and IMI, have slightly closer termini than the conotoxins shown in the top of the figure, which suggests cyclization would be more feasible for this class of conotoxins and may even occur more readily than that shown for MVIIA.

EXAMPLES

Example 1

A cyclic analogue of MVIIA (cyclo-MVIIA 1) has been synthesised with the sequence:—

SEQ ID NO. 5

CKGKGAKCSRLMYDCCTGSCRSGKCTRNGLPG

The residues in bold represent the sequence of MVIIA. Those not in bold are the linking moiety (TRNGLPG SEQ ID NO.: 1). A thioester method has been used in the synthesis of this peptide which was performed on a Gly PAM resin. A—$SCH_2$—$CH_2CO$— linker was attached to the Gly-PAM resin by treating the resin with bromopropanoic acid for 30 minutes, washing with DMF and then treating the resin with 10% thioacetic acid, 10% DIEA in DMF for 2×20 minutes. The resin was again washed with DMF and treated with 10% β-mercaptoethanol, 10% DIEA in DMF for 2×20 minutes. After a final wash with DMF, the first residue, Boc-glycine, wsa coupled to the resin using HBTU and DIEA. The remainder of the peptide was assembled by manual synthesis using HBTU with in situ neutralization (Schnölzer, M. et al., 1992).

The linker is not stable under basic conditions, thus the formyl group was not removed from the tryptophan with ethanolamine prior to HF cleavage. Cresol (800 μL) and thiocresol (200 μL) were used as scavengers during the HF cleavage which was carried out for 2 hours at −2 to 0° C. The crude, reduced peptide was purified using preparative reverse-phase HPLC on a Vydac C18 column. Gradients of 0.1% aqueous TFA and 90% acetonitrile/0.09% TFA were employed with a flow rate of 8 mL/min and the eluant monitored at 230 nm. The reduced peptide was cyclised in 0.1 M sodium phosphate (pH 7.4), with a 6 fold excess of TCEP at room temperature for 30 minutes. All linear material was cyclised within this time as judged by analytical reverse phase HPLC and mass spectrometry. Mass analysis was performed on a Sciex (Thornhill, Ontario) triple quadrupole mass spectrometer using electrospray sample ionization. Cyclo-MVIIA 1 was oxidized at a concentration of 0.5 mg/ml in 2M $(NH_4)_2SO_4$, 0.1 M $NH_4OAc$ (pH8) and 1 mM reduced glutathione at 4° C. for 24 hours. The product was purified using reverse phase preparative HPLC.

Example 2

A slightly smaller cyclic analogue of MVIIA (cyclo-MVIIA 2) has been synthesised with the sequence:—

SEQ ID NO. 6

CKGKGAKCSRLMYDCCTGSCRSGKCTRNG

Once again the bold residues correspond to the sequence of MVIA, (all except TRNG SEQ ID NO:2). This peptide was synthesised using the procedures outlined in Example 1. Following cyclisation, cyclo-MVIIA 2 was oxidised at a concentration of 0.5 mg/mL in 2 M $(NH_4)_2SO_4$, 0.1 M $NH_4OAc$ (pH 8) and 1 mM reduced glutathione at 4° C. for 24 hours. Three major components were present in the oxidation and were all purified using a semi-preparative C18 column (3 mL/min) with monitoring at 230 nm. The three components represent cyclic fully disulfide bonded forms of cyclo-MVIIA-2.

Example 3 a) Antagonists specific to N-type voltage-sensitive calcium channels are being used as leads in drug development. Examples of these are co-conotoxins GVIA and MVIIA. An assay has previously been established to determine the ability of a compound to displace $^{125}$I-GVIA from receptors in rat membrane. Rat membrane was prepared according to the procedure of Wagner et al. 1988. Rats were sacrificed by cervical dislocation and their brains removed and immediately frozen in liquid nitrogen. Frozen brains were stored at −78° C. until required. Three brains (wet weight, 6.25 g) were thawed (50 mM HEPES, pH 7.4) and homogenised with ultraturrex (IKA, 170 Watt) in 125 mls 50 mM HEPES pH 7.4. Homogenised brain was centrifuged at 16000 rpm (35000 g) for 20 min at 4° C. and the supernatant discarded. The pellet was resuspended by further homogenisation in 50 mM HEPES, pH 7.4, 10 mM EDTA and incubated at 4° C. for 30 min. Centrifugation was repeated as above and the supernatant discarded. The pellet was resuspended in 125 ml 50 mM HEPES, pH 7.4 (1:20 dilution) and stored at −78° C.

$^{125}$I-[Tyr22]GVIA was prepared according to the procedure of Cruz and Olivera (1986) and isolated by reverse-phase HPLC on an analytical Vydac C18 column. The column was equilibrated in buffer A (H$_2$O, 0.1% TFA) followed by a linear gradient to 67% buffer B (90% acetonitrile, 10% H$_2$O and 0.09% TFA) in 100 min. Peaks were detected at 214 nm and the flow rate was 1 ml/min. The radiolabeled peaks were counted using a gamma counter and stored at 4° C.

Assays were performed in 12×75 mm borasilicate culture tubes at room temperature and incubated for 1 hr. Each tube contained 100 μl each of test solution, iodinated ligand (7 fmol) and rat membrane (16 μg) added in this order. The assay buffer contained 20 mM HEPES pH7.2, 75 mM NaCl, 0.1 mM EDTA, 0.1 mM EGTA, 0.1% BSA and protease inhibitors, 2 mM leupeptin and 0.5 U aprotinin. The nonspecific binding was determined in the presence of 17 nM GVIA. Assays were terminated by vacuum filtration on a Millipore manifold filtration system using glass fibre filters (Whatman GFB) presoaked in 0.6% polyethylenimine. Each tube was washed 3 times with 3 ml ice-cold wash buffer (20 mM HEPES pH7.2, 125 mM NaCl and 0.1% BSA). Filters were counted on a gamma counter. Graphpad Prism was used to generate binding curves and calculate EC$_{50}$ values. The EC$_{50}$ values are a measure of the ability of a compound to displace $^{125}$I-GVIA; the EC$_{50}$ for MVIIA is 4.4×10.11 M. Fractions isolated from oxidation of the cysteine residues in cyclic, reduced cyclo-MVIIA 1 were tested in this assay. As expected, not all disulfide isomers had the same level of activity. The most active isomer exhibited an EC50 of 8.5×10−8 M. The three oxidized, cyclic forms of cyclo-MVIIA 2 were also tested in this assay and the most active isomer exhibited an EC50 of 5×10$^{-10}$ M. As expected, not all disulfide isomers had the same level of activity.

b) To test the specificity of the cyclic conotoxin derivatives for the N-type Ca channel relative to P/Q type channels additional binding studies were done using $^{125}$I-MVIIC as the displaced ligand. This binds selectively to P/Q type Ca channels.

The assay was carried out as described in Example 3a, except that $^{125}$I-MVIIC (selective for P/Q-type) channels was used as the displaced ligand rather than $^{125}$I-GVIIA (selective for N-type channels). The $^{125}$I-MVIIC was prepared and purified as described in Nielsen et al, 1999.

The most active form of cyclo-MVIIA 2 did not show any ability to displace $^{125}$I-MVIIC when administered at concentrations up to 630 nM. When combined with the data described above for displacement of $^{125}$I-GVIIA from N-type channels, this demonstrates selectivity for the N-type channel over the P/Q-type channel.

Example 4

Figure 3:
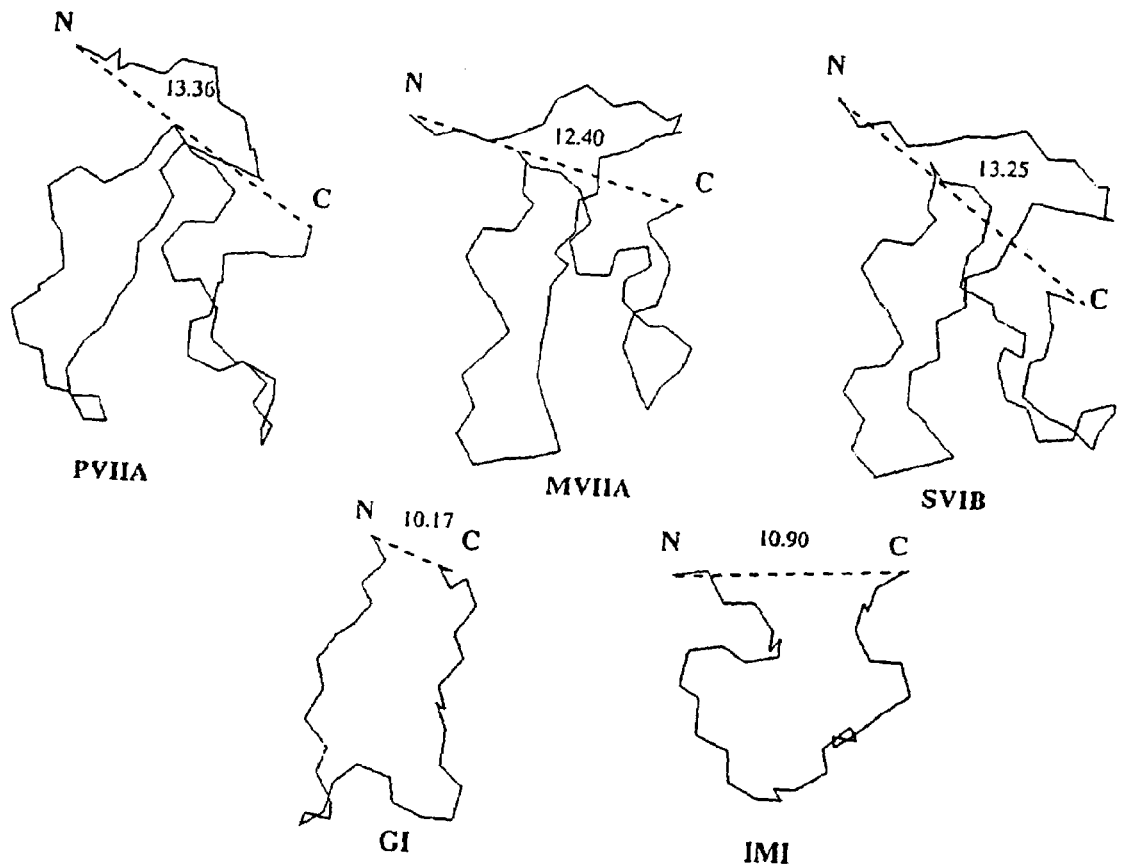

The three-dimensional structures of several conotoxin peptides have been determined by NMR spectroscopy to confirm the feasibility of making cyclic conotoxins which do not significantly alter the conformation of most parts of the conotoxin molecules. A comparison of five conotoxin structures determined by NMR is presented in FIG. 3.

Only the backbone atoms are displayed and the amino and carboxy termini are labelled as N and C respectively. The distances in angstroms between the termini have been measured and are also marked on the diagram. The three structures in the top half of the diagram represent PVIIA (Scanlon et al., 1997), MVIIA (Nielsen et al., 1996) and SVIB (Nielsen et al., 1996). It is clear that in all three peptides the overall structure is very similar, as is the distance between the termini. MVIIA and SVIB are both classed as omega conotoxins and have some sequence homology (Table 1), however PVIIA belongs to the kappa class and has little sequence homology to MVIIA and SVIB except for the conserved cysteine residues. It has now been shown that MVIIA can by cyclised and still retain a high level of activity (Examples 1–3). Given the structural similarity between the peptides mentioned above, cyclisation is feasible for other conotoxins, such as PVIIA and SVIB.

The alpha conotoxins have a different structure than the previously mentioned peptides, however the termini are still close, as shown for GI (Gehrmann et al., 1998) and IMI (unpublished data) above. The close proximity of the termini suggests cyclisation can be achieved without significantly affecting the biological activity. Thus, the concept of cyclising conotoxins is applicable not only to omega conotoxins but to peptides from other classes of conotoxins, including alpha and kappa, and extends to all conotoxins which have termini located close together, especially those within a distance of approximately 13 Å (i.e. the distance present in MVIIA).

In the case of mu-conotoxins the termini are further apart in general, but cyclisation is readily possible using longer peptide sequences as linkers. In the case of Na-channel conotoxins like GS the peptide contains a C-terminal extension beyond the final cysteine residue that may form part of the cyclising linker.

Example 5

To exemplify the principles involved in synthetic method 2 described above an analogue of MVIIA has been synthesised using solid phase peptide synthesis with Boc chemistry. The synthesised peptide has the sequence:

SEQ ID NO. 7

GLPVCKGKGAKCSRLMYDCCTGSCRSGKCTRG

The peptide has both an N(GLPV) and C(TRG) terminal extension and the remaining residues (in bold) represent MVIIA. The reduced peptide was purified using the conditions given in Examples 1 and 2. Oxidation was achieved using 0.1 M ammonium acetate, 2M ammonium sulfate, pH 7.7, 1 mM reduced glutathione and the reaction left at 4° C. for two days. The oxidised peptide was purified and the activity tested as in Example 3. An EC$_{50}$ of 1.081×10$^{-9}$ M was found for this analogue, illustrating that extending the N and C termini of the peptide, as may be necessary prior to cyclisation, does not eliminate activity.

Example 6

A cyclic α-conotoxin is prepared based on the sequence of α-conotoxin MII. The linear precursor for this synthesis is designed by first adding a linker moiety to the native sequence as shown below. The residues in bold correspond to the native sequence of MII and the non-bold residues are the linker moiety (TNG SEQ ID NO: 4).

SEQ ID NO. 8

GCCSNPVCHLEHSNLCTNG

A cyclically permuted derivative of this sequence is then designed by moving the N-terminal glycine residue to the C-terminus to produce the sequence:

SEQ ID NO. 9

CCSNPVCHLEHSNLCTNGG

Thi peptide is synthesised using the thioester method described above in which the C-terminal glycine is attached to a Gly PAM resin via a —SCH$_2$CH$_2$CO— linker. The linker is attached to the Gly PAM resin by treating the resin with bromopropanoic acid for 30 minutes, washing with DMF and then treating the resin with 10% thioacetic acid, 10% DIEA in DMF for 2×20 minutes. The resin is washed again with DMF and treated with 10% β-mercaptoethanol, 10% DIEA in DMF for 2×20 minutes. After a final wash with DMF, the first (ie C-terminal) residue of the linear peptide sequence is coupled to the resin using HBTU and DIEA. The remainder of the peptide sequence is assembled by manual synthesis using HBTU with in situ neutralisation. Cleavage from the resin, cyclisation and oxidation is achieved using the methods described in Examples 1 and 2.

Example 7

The bioavailability of cyclic conotoxins is tested by either oral administration or intravenous administration into rats. Male Sprague-Dawley-derived rats (ca. 325 g) are maintained on standard rat pellets until surgery, and are subsequently prepared, under isoflurane anaesthesia, with a catheter in the right external jugular vein. Rats are then placed unrestrained n metabolism cages and allowed to recover prior to dosing. A 75 mm oral dosing (gavage) needle is used to dose conscious rats and the jugular catheter is used for iv dosing. Following dosing, plasma samples are taken out at time points between 0 and 180 min. A blood sample (ca. 500 mL) is withdrawn and centrifuged and then placed on ice until processing. The supernatant (200 mL) is transferred and HPLC grade acetonitrile (300 mL) added to precipitate proteins, however the test peptides remain in solution. The sample is then centrifuged and the supernatant transferred for further analysis. The supernatant is diluted with 0.1% TFA and injected on to an analytical reverse phase C 18 column using gradients of 0.1% TFA/0.9% TFA in 90% acetonitrile: 10% water. The eluent is monitored at 214 nm. This analysis allows calculation of a half-life for the peptide of interest.

Further studies are performed to give indications of stability of cyclic conotoxins in biological media and hence an indication of bioavailability. Biological media such as fetal calm serum and rat gastric juices are used. The cyclic conotoxin solution (10 mL 1 mg/mL) is diluted with 0.1 M PBS pH 7.6 (~50 mL) and fetal calm serum (~50 mL) is added to the sample. The sample is then incubated at 37° C. for ~1–5 hours. An aliquot (~40 mL) is removed and diluted with 0.1% TFA and injected on an analytical C18 reverse phase HPLC column with gradients of 0.1% TFA/0.9% TFA in acetonitrile. The sample is monitored at 214 nm. The stock peptide solution, appropriately diluted, is used as a control and allows the percentage breakdown at a particular timepoint to be calculated. A similar protocol is applied for rat gastric juices. However, the peptide is not diluted in buffer but incubated at 37° C. for 1–5 hours and aliquots analyzed by reverse phase HPLC. Performing these studies on linear and cyclic conotoxins shows the greater stability of the cyclic conotoxins.

REFERENCES

Cruz, L. J. and Olivera, B. M. (1986). Calcium channel antagonists. Omega-conotoxin defines a new high affinity site J. Biol. Chem. 261, 6230–6233.

Gehrmann J., Alewood P. F., & Craik D. J. (1998) Structure determination of the three disulfide bond isomers of alpha-conotoxin GI—A model for the role of disulfide bonds in structural stability. J. Mol. Biol. 278, 401415.

Hill J M, Alewood P F, Craik D J: Solution structure of the sodium channel antagonist conotoxin GS: a new molecular caliper for probing sodium channel geometry. Structure (1997) 5, 571–583.

Hopkins, C., Grilley, M., Miller, C., Shon, K., Cruz, L. J., Gray, W. R., Dykert, J., Rivier, J., Yoshikami, D. & Olivera, B. M. (1995). A new family of *Conus* peptides targeted to the nicotinic acetylcholine receptor. J. Biol. Chem. 270, 22361–22367.

Myers, R. A., Cruz, L. J., Rivier, J. E. & Olivera, B. M. (1993). *Conus* peptides as chemical probes for receptors and ion channels. Chem. Rev. 93, 1923–1936.

Myers, R. A., McIntosh, J. M., Imperial, J., Williams, R. W., Oas, T., Haack, J. A., J., H., Rivier, J., Cruz, L. J & Olivera, B. M. (1990). Peptides from *Conus* venoms which affect Ca$^{++}$ entry into neurons. J. Toxicol.—Toxin Reviews. 9, 179–202.

Nielsen K J. Adams D, Thomas L, Bond T, Alewood P F, Craik D J, Lewis R J: Structure-activity relationships of w-conotoxins MVIIA, MVIIC and 14 loop splice hybrids at N- and P/Q-type calcium channels. J Mol Biol (1999) 289, 1405–1421.

Nielsen K. J., Thomas K., Lewis R. J., Alewood P. F., & Craik D. J. (1996) A consensus structure for omega-conotoxins with different selectivities for voltage-sensitive calcium channel subtypes—comparison of MVIIA, SVIB AND SNX-202. J. Mol. Biol. 263, 297310.

Olivera, B. M., Rivier, J., Clark, C., Ramilo, C. A., Corpuz, G. P., Abogadie, F. C., Mena, E. E., Woodward, S. R., Hillyard, D. R. & Cruz, L. J. (1990). Diversity of Conus neuropeptides. Science. 249 248–263.

Olivera, B. M., Rivier, J., Scott, J. K., Hillyard, D. R. & Cruz, L. J. (1991). Conotoxins J. Biol. Chem. 266, 22067–22070.

Scanlon M. J., Naranjo D., Thomas L., Aleqood P. F. Lewis R. J., & Craik D. J. (1997) Solution structure and proposed binding mechanism of a novel potassium channel toxin kappa-conotoxin PVIIA. Structure 5, 1585–1597.

Schnolzer, M., Alewood, P., Jones, A., Alewood, D. & Kent, S. B. H. (1992). In situ neutralization in Boc-chemistry solid phase peptide synthesis. Int. J. Pept. Prot. Res. 40, 180–193.

Wagner, J. A., Snowman, A. M., Biswas, A., Olivera, B. M. and Snyder, S. H. (1988). Omega-conotoxin GVIA binding to a high-affinity receptor in brain: characterization, calcium sensitivity, and solubilization. J. Neuroscience 8, 3343–3359.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A synthetically cyclised α- or ω-conotoxin peptide having an amide cyclised backbone such that the peptide has no free N- or C-terminus, said conotoxin peptide comprising either 4 cysteine residues which are bonded in pairs to form two disulfide bonds or 6 cysteine residues which are bonded in pairs to form three disulfide bonds, wherein said cyclised α-conotoxin peptide has α-conotoxin peptide activity and said cyclised co-conotoxin peptide has ω-conotoxin peptide activity.

2. The cyclic conotoxin peptide according to claim 1 which comprises or consists of the sequence of amino acids present in a naturally occurring conotoxin peptide.

3. The cyclic conotoxin peptide according to claim 2 wherein the naturally occurring conotoxin peptide comprises the amino acid sequence as set forth in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, SEQ ID NO: 23, or SEQ ID NO: 24.

4. The cyclic conotoxin peptide according to claim 1 having three disulphide bonds in the form of a cysteine knot.

5. The cyclic conotoxin peptide according to claim 1 comprising an amino acid sequence of a linear conotoxin peptide and a peptide linker, wherein the N- and C-termini of the amino acid sequence are linked via the peptide linker to form an amide cyclised peptide backbone.

6. The cyclic conotoxin peptide according to claim 5 wherein the linear conotoxin peptide is a naturally occurring conotoxin peptide and the cyclic conotoxin peptide retains the disulphide bond connectivity of the naturally occurring conotoxin peptide.

7. The cyclic conotoxin peptide according to claim 5 wherein the peptide linker is from 2 to 15 amino acids in length.

8. The cyclic conotoxin peptide according to claim 5 wherein the peptide linker is selected from the group consisting of:

TRNGLPG           SEQ ID NO:1

TRNG              SEQ ID NO:2

TRGGLPV           SEQ ID NO:3, and,

TNG               SEQ ID NO:4.

9. The cyclic conotoxin peptide according to claim 1 selected from the group consisting of:

CKGKGAKCSRLMYDCCTGSCRSGKCTRNGLPG     SEQ. ID NO. 5

CKGKGAKCSRLMYDCCTGSCRSGKCTRNG        SEQ. ID NO. 6

GLPVCKGKGAKCSRLMYDCCTGSCRSGKCTRG     SEQ ID NO.7

GCCSNPVCHLEHSNLCTNG ,   and          SEQ ID NO. 8

CCSNPVCHLEHSNLCTNGG                  SEQ ID NO. 9

10. A pharmaceutical composition comprising a cyclic conotoxin peptide according to claim 1 and a pharmaceutically acceptable carrier or diluent.

11. The cyclised conotoxin peptide of claim 1 wherein said conotoxin peptide is an ω-conotoxin and said cyclised conotoxin peptide has α-conotoxin peptide activity.

12. The cyclised conotoxin peptide of claim 1 wherein said conotoxin peptide is an α-conotoxin peptide and said cyclised conotoxin peptide has α-conotoxin peptide activity.

13. A process for preparing the cyclic conotoxin according to claim 1 comprising:
   (i) synthesizing an extended linear conotoxin peptide on a solid phase support, said extended linear conotoxin peptide comprising a linear conotoxin peptide having a linker moiety attached to at least one end thereof
   (ii) cleaving said extended linear peptide from the support (iii) cyclising said extended linear conotoxin peptide, and
(iv) oxidizing said cyclised peptide to form disulphide bonds.

14. A process for preparing the cyclic conotoxin according to claim 1 comprising:
  (i) synthesizing an extended linear conotoxin peptide on a solid phase support, said extended linear conotoxin peptide comprising a linear conotoxin peptide having a linker moiety attached to at least one end thereof,
  (ii) cleaving said linear peptide from the solid support,
  (iii) subjecting said extended peptide to conditions such that the peptide folds and forms the required disulphide bands, and
  (iv) cyclising the folded peptide.

15. A method for treating pain in a mammal comprising the step of administering to the mammal an amount of the cyclic conotoxin peptide of claim 1 effective to treat pain in the mammal.

16. A method for treating stroke in a mammal comprising the step of administering to the mammal an amount of the cyclic conotoxin peptide of claim 1 effective to treat stroke in the mammal.

17. A method for treating traumatic brain injury in a mammal comprising the step of administering to the mammal an amount of the cyclic conotoxin peptide of claim 1 effective to treat traumatic brain injury in the mammal.

18. A method of blocking a voltage-sensitive calcium channel in a mammal comprising administering to the mammal an amount of the conotoxin peptide according to claim 1 effective to block the voltage-sensitive calcium channel.

19. A method of blocking the nicotinic acetylcholine receptor in a mammal comprising administering to the mammal an amount of the conotoxin peptide according to claim 1 effective to block the nicotinic acetylcholine receptor.

20. A method of probing an ion channel receptor comprising contacting said ion channel receptor with the cyclic conotoxin peptide according to claim 1; and measuring a biological effect the cyclic conotoxin peptide has on the ion channel receptor.

* * * * *